United States Patent [19]
Huebner

[11] Patent Number: 5,234,430
[45] Date of Patent: Aug. 10, 1993

[54] ORTHOPEDIC FIXATION SCREW AND METHOD

[76] Inventor: Randall J. Huebner, 18560 SW. Hart, Aloha, Oreg. 97007

[21] Appl. No.: 812,138
[22] Filed: Dec. 18, 1991
[51] Int. Cl.$^5$ ............................................. A61F 5/00
[52] U.S. Cl. ...................................... 606/60; 606/72
[58] Field of Search ...................... 606/72, 73, 60, 61, 606/104

[56] References Cited

U.S. PATENT DOCUMENTS

| | | | |
|---|---|---|---|
| 2,382,019 | 8/1945 | Miller | 606/72 X |
| 3,741,205 | 6/1973 | Markolf et al. | 606/61 |
| 4,041,939 | 8/1977 | Hall | 606/61 X |
| 4,632,100 | 12/1986 | Somers et al. | 128/92 |
| 4,772,286 | 9/1988 | Goble et al. | 623/13 |
| 4,870,957 | 10/1989 | Goble et al. | 128/92 |
| 4,927,421 | 5/1990 | Goble et al. | 606/73 |
| 4,950,270 | 8/1990 | Bowman | 606/72 |
| 5,019,080 | 5/1991 | Hemer | 606/104 X |

FOREIGN PATENT DOCUMENTS 643131  5/1984  Switzerland .......................... 606/73

OTHER PUBLICATIONS

M. Kurosaka brochure, "Interference Fixation Screw System".

"Pitfalls in the Use of Interference Screws for Anterior Cruciate Ligament Reconstruction: Brief Report", by L. S. Matthews, MD and S. R. Soffer, MD, Arthroscopy: The Journal of Arthroscopic and Related Surgery, vol. 5, No. 3, Raven Press, Ltd, 1989, pp. 225–226.

"Potential Pitfalls of Kurosaka Screw Interference Fixation for ACL Surgery", B. R. Bach, Jr., M.D., The American Journal of Knee Surgery, vol. 2, No. 2, Apr. 1989, pp. 76–82.

"Tensile Strength of Soft Tissue Fixations About the Knee", Marty Ivey, M.D. and Fan Li, M.D., The American Journal of Knee Surgery, vol. 4, No. 1, Jan. 1991, pp. 18–23.

"A Biomechanical Comparison of Different Surgical Techniques of Graft Fixation in Anterior Cruciate Ligament Reconstruction", M. Kurosaka, M.D., et al., The American Journal of Sports Medicine, vol. 15, No. 3, 1987, pp. 225–229.

Howemedica brochure, "Specialty Screws".

*Primary Examiner*—Robert A. Hafer
*Assistant Examiner*—Sam Rimell
*Attorney, Agent, or Firm*—Marger, Johnson, McCollom & Stolowitz

[57] ABSTRACT

An orthopedic fixation screw for anchoring a bone graft in a bore formed in a bone mass. An elongate cylindrical nose portion has a substantially smooth outer surface for being received without interference into the space between the graft and a wall of the bore. A threaded portion interferingly engages the graft and a wall of the bore as said threaded portion is rotated when the nose portion is so received. An hexagonal socket in the rear of the screw receives either a driver having tapered hexagonal walls for tightly receiving the screw on the driver during installation or a conventional hex driver for removing an installed screw in the event the tapered driver is unavailable when the screw is to be removed.

2 Claims, 2 Drawing Sheets

ORTHOPEDIC FIXATION SCREW AND METHOD

BACKGROUND OF THE INVENTION

1. Field of the Invention

The present invention relates to orthopedic fixation screws and methods and more particularly to such screws and methods in which a bone graft is anchored in a bore formed in a bone mass.

2. Description of the Related Art

The anterior cruciate ligament (ACL) is 25 mm–40 mm in length and is frequently injured in contact and other activities. Such injuries can cause instability in the knee to the extent that ACL reconstruction may be required.

The replacement of the ACL with the central third of the patellar tendon using a bone-tendon-bone graft is a known method for restoring knee stability. In this procedure, the central third of the patellar tendon and portions of bone at either end thereof are taken as a graft. A tunnel is bored in the distal femur and proximal tibia, i.e., where they join at the knee. The bone-tendon-bone graft is disposed with one bone segment in one of the tunnels and the other bone segment in the other tunnel. With the graft so disposed, each of the bone segments are anchored by screwing an interference screw into the tunnel between a tunnel wall and the bone segment thereby anchoring the segment in the tunnel.

Such procedure is illustrated and described in U.S. Pat. No. 4,927,421 to Goble et al. for process of endosteal fixation of a ligament. The Goble et al. method suffers from several disadvantages. First, the interference screw is cannulated, i.e., it has an axial bore for riding a guide wire into the bore. The wire must be inserted into the bore adjacent the bone graft before the screw can be installed. The guide wire prevents divergence of the screw as it is screwed into the space between the graft and the tunnel wall. A special driver, also having an axial bore for receiving the guide wire, must be provided to install the screw. Threading the wire through the bore is an additional surgical step, in itself undesirable, which has the potential for creating metal debris. In addition, the guide wires can bend or kink. The screw of the Goble et al. application provides an extremely steep taper at the leading end thereof which rapidly compresses the graft as the screw is installed.

SUMMARY OF THE INVENTION

The present invention comprises an orthopedic fixation device for anchoring a bone graft in a bore formed in a bone mass. The screw includes an elongate cylindrical nose portion for being received without interference into the space between the graft and the wall of the bore. The threaded portion on the screw interferingly engages the graft and a wall of the bore as the threaded portion is rotated when the nose portion is so received.

The present invention obviates the need for using a cannulated interference screw and further provides improved gradual compression of the graft as the fixation screw is installed.

The foregoing and other objects, features and advantages of the invention will become more readily apparent from the following detailed description of a preferred embodiment which proceeds with reference to the drawings.

DETAILED DESCRIPTION OF THE PREFERRED EMBODIMENT

Figure 1:
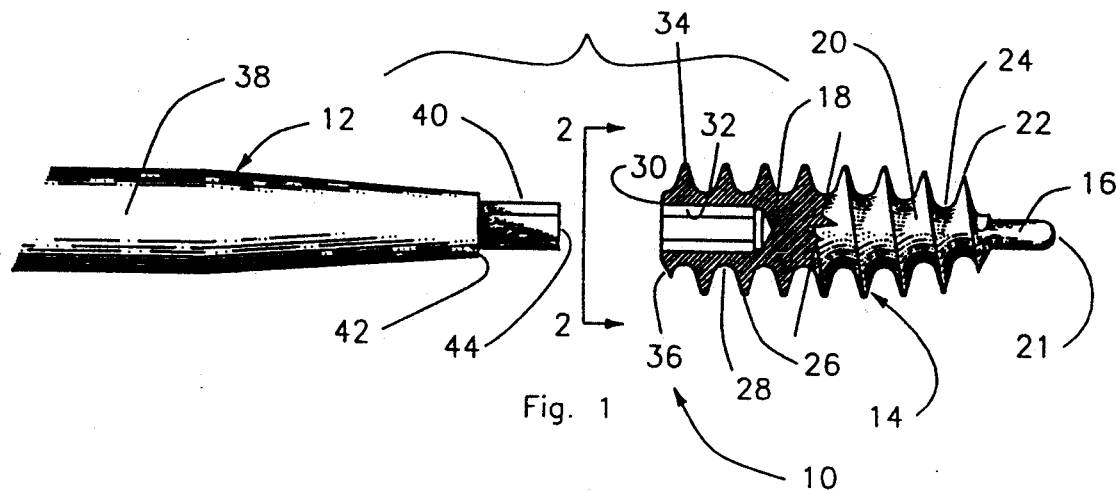
FIG. 1 is an enlarged view, partly in cross-section, of an orthopedic fixation screw and a portion of a driver therefor constructed in accordance with the present invention.

Turning first to FIG. 1, indicated generally at 10 is an orthopedic fixation device for anchoring a bone graft in a bore formed in a bone mass. Device 10 includes a driver 12 and a screw 14. The screw includes an elongate nose portion or nose 16, a threaded body portion 18 and a threaded tapered portion 20 which extends between the nose and the body portion. Nose 16 includes a hemispherical leading face 21. The nose is preferably at least twice the length of the diameter of the nose. The tapered portion 20 extends for approximately three complete threads from nose 16 to threaded body portion 18. As can be seen in FIG. 1, threaded body portion 18 has a cylindrical root while threaded tapered portion 20 has a root which tapers from the body portion to nose 16. Because the root is tapered as shown, the distance between thread crest 22 and root portion 24 on the tapered part of the root is substantially the same distance as between thread crest 26 and root portion 28 on the cylindrical part of the root. The present embodiment of screw 14 has a uniform pitch of ten threads per inch along the threaded portion thereof.

Figure 2:
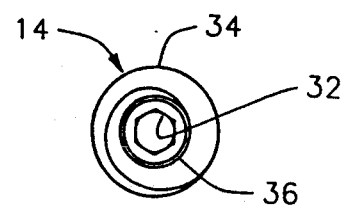
FIG. 2 is a view along line 2—2 in FIG. 1.

A rear surface 30 of screw 14 includes an axial hexagonal socket 32. The socket walls are parallel to the axis of screw 14 and are sized to receive a conventional hexagonal driver. The height of the thread crest becomes progressively less between about thread crest 34 and rear surface 30 of the screw. A substantially 30° chamfer 36 is formed at the juncture between rear surface 30 and the root of threaded body portion 18. The progressive reduction of thread crest height thus forms a spiral between crest 34 and chamfer 36 as viewed in FIG. 2.

Driver 12 includes a shaft 38 having a driving end 40 formed on one end and a handle (not shown), similar to the handle of a screw driver, formed on the other end thereof. Driving end 40 comprises a hexagonal driver having walls which taper inwardly between the juncture 42 of driving end 40 with shaft 38 and the outer end 44 of driving end 40. As can be seen in FIG. 1, the distance between juncture 42 and end 44 is slightly less than the depth of socket 32. The relative sizes of driving end 40 and socket 32 are such that the hexagonal walls of driving end 40 engage the interior walls of socket 32 as the screw socket is fitted over driving end 40. Such engagement occurs just before rear surface 30 reaches juncture 42. Given that the interior walls of socket 32 are substantially parallel to the longitudinal axis of driver 12 while the walls of driving end 40 taper as described above, the screw can be fitted onto the end of driver 12 by pushing the screw until driving end 40 and socket 32 are tightly engaged.

Figure 3:
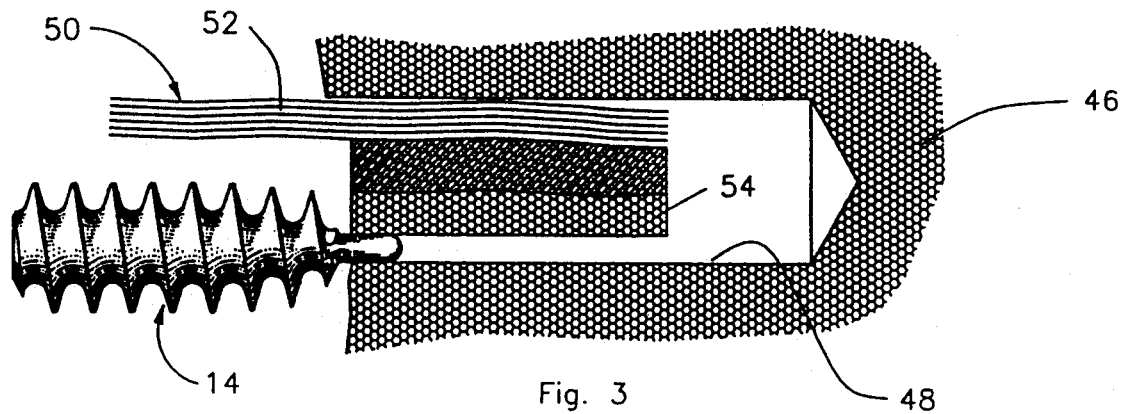
FIG. 3 is a view, partly in cross-section, of the screw of FIG. 1 with the nose thereof disposed between a bone graft and the wall of a bore in a bone mass.

Turning now to FIG. 3, a bone mass 46 has a bore 48 formed therein. In the case of ACL reconstructive surgery, the bore is formed in either the distal femur or proximal tibia, or both when screw 14 is used to anchor both ends of a bone-tendon-bone graft. Bore 48 is also referred to herein as an endosteal tunnel. One end of a bone-tendon-bone graft 50 is shown received in bore 48. Graft 50 includes a tendon 52 and a bone portion 54 connected to the tendon. The other end of tendon 52 (not shown) similarly includes a bone portion connected thereto.

In use, an orthopedic surgeon bores a hole in bone mass 46 which, for purposes of the present explanation is assumed to be the distal femur. This is accomplished using a conventional orthopedic drill and may be done endoscopically as may be the remainder of the following-described procedure. After bore 48 is drilled as shown in FIG. 3, one end of graft 50 is positioned in the bore as illustrated. Screw 14 is fitted onto driver 12 as described above so that socket 32 is firmly engaged with driving end 40. The surgeon grasps driver 12 by its handle (not shown) and positions screw 14 as illustrated in FIG. 3, i.e., nose 16 is received in the space between bone portion 54 and the interior wall of bore 48. Nose 16 is referred to herein as being received without interference into the space between the graft and a wall of the bore. This describes the relative sizes of the nose and the gap between bone 54 and bore 48 and the fact that when screw 14 is positioned as shown in FIG. 3, no threads are engaged with either bone 54 or bore 48.

Figure 4:
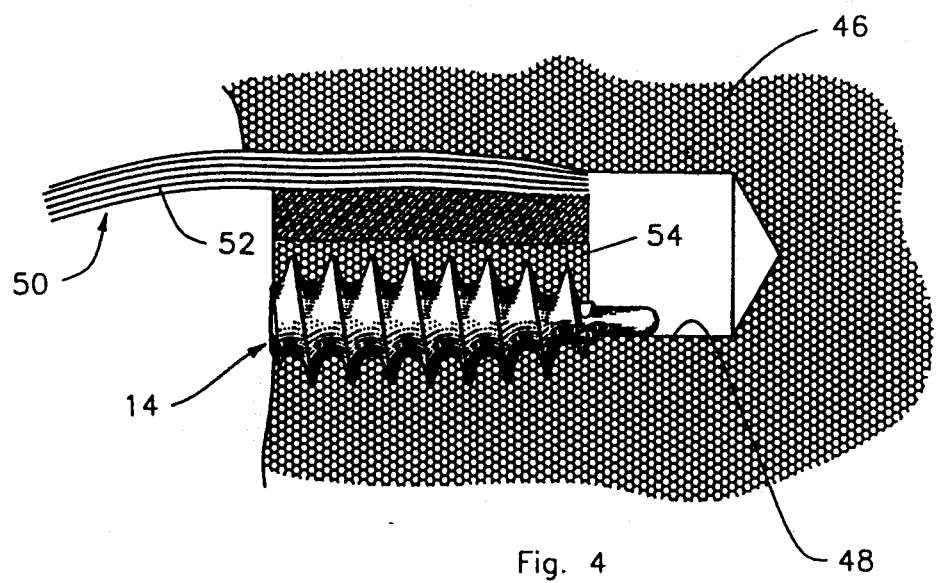
FIG. 4 is a view similar to FIG. 3 after the screw is fully installed.

Next, the surgeon pushes axially toward the screw on the handle of driver 12 and begins rotation of the driver handle thereby causing the threads to engage the inner wall of bore 48 and bone portion 54. As threaded tapered portion 20 advances, the tapered root enters the space between bone portion 54 and bore 48 thereby gradually compressing bone portion 54 against the other side of the bore. As the tapered root advances, such compression gradually increases until the screw is positioned as shown in FIG. 4. When enough of screw 14 is advanced to compress bone portion 54 against the bore and retain the same therein, bone portion 54 is anchored by an interference fit between the screw and bore 48.

Once the screw is positioned as shown in FIG. 4, the surgeon may withdraw driver 12 by gently rocking the driver and pulling the handle so as to withdraw driving end 40 from socket 32. It should be noted that if it becomes necessary to remove the screw during a later surgical procedure, socket 32 cooperates with a standard hex driver. If a driver, like driver 12, is not available when the screw is to be removed, it may be removed with a standard hex driver.

Another screw, like screw 14 can be used in a corresponding bore in the proximal tibia (not shown) to anchor the other end of graft 50 in a similar manner to that described above for anchoring the graft in the distal femur.

Because of the tapered root, the threads are able to gain purchase at a relatively narrow portion of the root so that graft shifting or twisting during installation is less likely to occur than with prior art screws. Nose 16 thus aligns screw 14 as illustrated in FIG. 3 and maintains the alignment as the threads are advanced into the bone. Because the tapered root reduces the force which must be applied to the screw to engage the first several threads, the nose is sufficient to maintain alignment of the screw. It is therefore not necessary to provide the screw of the present invention with an axial bore having a guide wire received therethrough to prevent screw divergence as it is installed.

Having illustrated and described the principles of my invention in a preferred embodiment thereof, it should be readily apparent to those skilled in the art that the invention can be modified in arrangement and detail without departing from such principles. I claim all modifications coming within the spirit and scope of the accompanying claims.

I claim:

1. A method for securing a bone graft in an endosteal tunnel comprising the steps of:

drilling an endosteal bore of a size sufficient to form a space between said bone graft and a wall of the bore when said graft is inserted in said bore, said bore having an open end and a closed end;

inserting the graft in the open end of the bore;

providing an uncannulated bone screw having a cylindrical elongate nose, a substantially hemispherical leading face, and a tapered root adjacent said nose, said nose having a diameter less than the root diameter and further having a smooth surface adapted for sliding without rotation and without cutting bone into said space with said bore wall and said graft abutting said nose;

orienting the longitudinal axis of the bone screw responsive to fully inserting the nose thereof into said space without rotation and without cutting bone while said bore wall and said graft abut said nose;

thereafter rotating said screw until the threads thereon begin to engage said bone graft and said bore wall; and continuing screw rotation until the threads of said screw fully engage said bone graft and said bore wall thereby fixing said graft in said bore.

2. The method of claim 1 wherein said bone screw further includes a cylindrical root portion adjacent said tapered root and where the thread depth on said tapered root is substantially the same as the thread depth on said cylindrical root portion.

* * * * *